Figure 1:
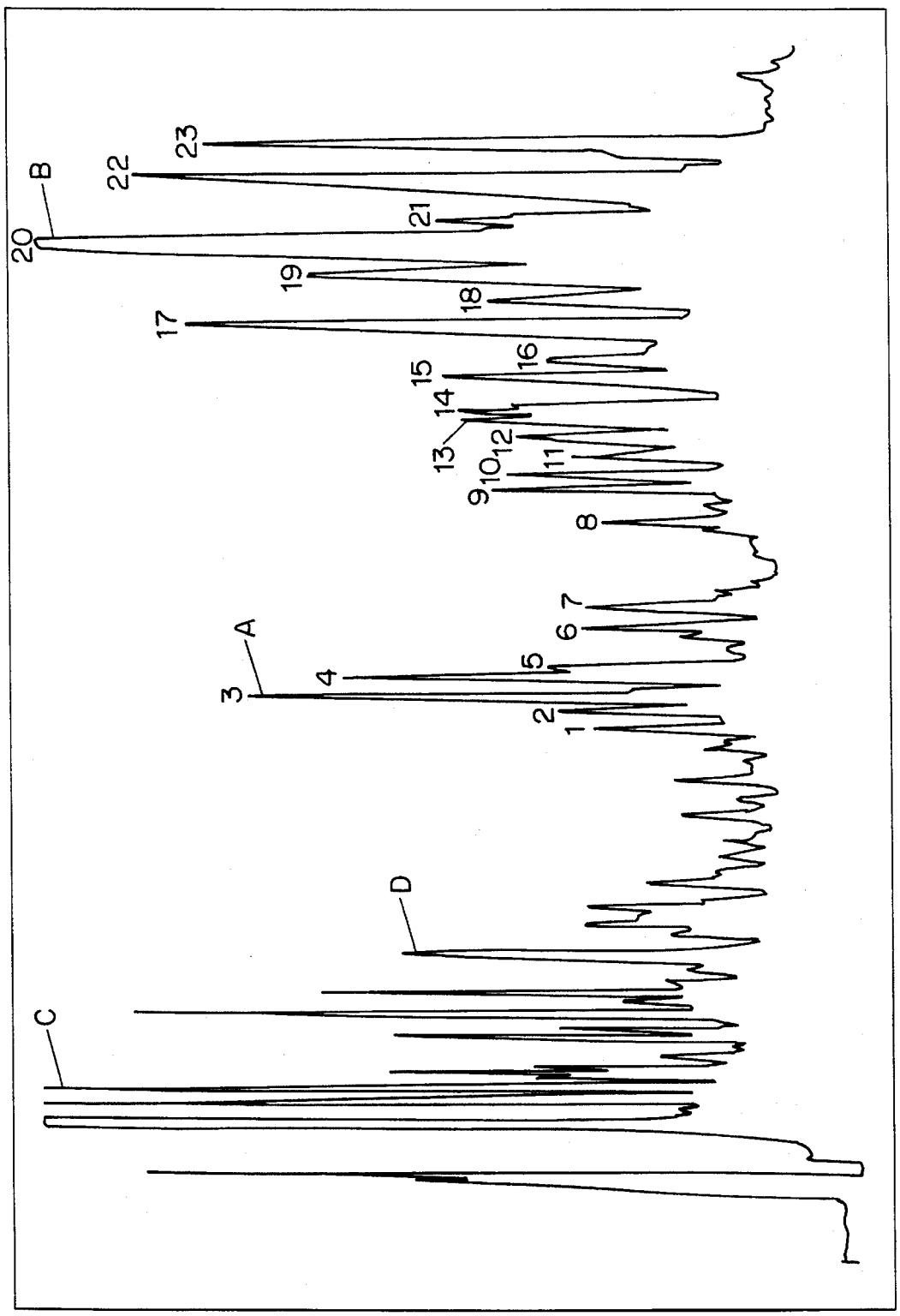

United States Patent [19]

Kersten et al.

[11] Patent Number: 5,620,690
[45] Date of Patent: Apr. 15, 1997

[54] IMMUNOGENIC COMPLEXES

[75] Inventors: Gideon F. A. Kersten, Utrecht; Arjan Spiekstra, Nieuwegein; Gerrit Van Der Werken, Utrecht; Eduard C. Beuvery, Vianen, all of Netherlands

[73] Assignee: De Stat Der Nederlanden Vertegenwoordigd Door De Minister Van Welzijn Volksgezondheid En Cultuur, Rijswijk, Netherlands

[21] Appl. No.: 39,294
[22] PCT Filed: Oct. 23, 1991
[86] PCT No.: PCT/NL91/00211
§ 371 Date: Apr. 19, 1993
§ 102(e) Date: Apr. 19, 1993
[87] PCT Pub. No.: WO92/06710
PCT Pub. Date: Apr. 30, 1992

[30] Foreign Application Priority Data

Oct. 23, 1990 [NL] Netherlands ............... 9002314

[51] Int. Cl.$^6$ ............... C07G 3/00; A61K 39/00; C07H 15/24; C07H 17/00
[52] U.S. Cl. ............... 424/184.1; 536/41; 536/5; 536/6.3; 424/489
[58] Field of Search ............... 536/4.1, 5, 6.3; 424/88, 89, 92, 184.1, 489

[56] References Cited

U.S. PATENT DOCUMENTS

| | | | |
|---|---|---|---|
| 4,578,269 | 3/1986 | Morein | 424/88 |
| 4,744,983 | 5/1988 | Morein | 424/88 |
| 4,900,549 | 2/1990 | DeVries et al. | |
| 4,981,684 | 1/1991 | MacKenzie et al. | 424/88 |
| 5,057,540 | 10/1991 | Kensil et al. | 514/25 |
| 5,254,339 | 10/1993 | Morein | 424/88 |
| 5,273,965 | 12/1993 | Kensil et al. | 514/3 |

FOREIGN PATENT DOCUMENTS

WO88/09336 12/1988 WIPO.
WO90/03184 4/1990 WIPO.

OTHER PUBLICATIONS

Buroru, Morein, "Adjuvant–Lipid Complexes for Use as Modified Adjuvants in Preparing Vaccines", *Chemical Abstracts*, vol. 113, No. 21, Abstract No. 189646f, Nov. 1990, p. 573.
Kersten et al. (1988) Infection and Immunity 56(2) 432–438.
Morein et al. (1987) Immunolog Today 8(11):333–338.

Primary Examiner—James C. Housel
Assistant Examiner—N. M. Minnifield
Attorney, Agent, or Firm—Brumbaugh, Graves, Donohue & Raymond

[57] ABSTRACT

The invention relates to immunogenic complexes such as two-dimensional lamellae having a honeycomb structure and in particular three-dimensional iscoms, which immunogenic complexes are composed of at least one sterol, one saponin and, in the case of iscoms, also a phospholipid and also, optionally, at least one antigen generating an immune reaction. The saponin used is at least one of the fractions which are derived from Quil A by means of hydrophobic interaction chromatography and have the designations QA 1 to QA 23, as is shown in the figure by the numerals 1 to 23. Preferably, the saponin used is one or more of the fractions derived from Quil A having the designations QA 3, QA 17 and QA 23. As well as relating to the immunogenic complex, the invention also relates to the specific method of preparation of the relevant Quil A fractions, to vaccines which contain such immunogenic complexes and to kits which contain, on the one hand, an (empty) immunogenic complex and, on the other hand, one or more antigenic proteins or peptides having a hydrophobic fragment which may or may not have been synthetically introduced.

10 Claims, 9 Drawing Sheets

IMMUNOGENIC COMPLEXES

The invention relates to immunogenic complexes such as two-dimensional lamellae having a honeycomb structure and in particular three-dimensional iscoms, which complexes are composed of at least one sterol, one saponin and, in the case of an iscom, also a phospholipid, as well as, optionally, at least one antigen generating an immune reaction.

EP-A-87,200,035.1 discloses a method for the preparation of immunogenic complexes, in which method an antigenic protein or peptide in dissolved or solubilised form is brought into contact with a solution which contains a detergent, a glycoside having a hydrophobic and a hydrophilic fragment, in at least the critical micelle-forming concentration (CMC), and also a sterol, the detergent is then removed and the immunogenic complex formed is purified. If the immunogenic complex formed is to have an "iscom" form, that is to say a cage-like structure which is built up from sub-units and has a diameter of about 35 nm or greater, a phospholipid must also be present in the abovementioned solution of the detergent, glycoside and sterol.

In the method according to this EP-A, saponins, such as saponins from *Quillaja saponaria* Molina, *Aesculus hippocastanum* or *Gypsophilia struthium*, are advantageously used as glycoside. Preferably, the product "Quil A" is used, this being a water-soluble extract from the bark of *Quillaja saponaria* Molina (K. Dalsgaard: Saponin Adjuvants III, Archiv für die gesamte Virusforschung 44, 243–254 (1974)). More particularly, Quil A is a mixture of saponins of the triterpene class. Although Quil A lipid complexes and the like are regarded as effective antigen adjuvants essentially for amphipathic antigens, the mode of administration of complexes of this type is severely limited by the toxicity of Quil A. In this context, it is pointed out that, specifically, the toxicity of Quil A-containing immunogenic complexes is considered undesirably high for administration via, inter alia, the intraperitoneal (i.p.) route. This toxicity associated with Quil A is in all probability due to the haemolytic activity of this product.

WO 90/03184 discloses iscom matrices having an immunomodulatory activity. More particularly, this WO application relates to matrices which are composed of at least one lipid and at least one saponin. Advantageously, the lipid used is cholesterol. Examples of saponins are, in particular, triterpene saponins, preferably Quil A or one or more components of Quil A, which are indicated by the designations B4B, B2 and B3. With regard to the three abovementioned Quil A components, it is stated in WO 90/03184 that B4B, which has a molecular weight of 1862, is indeed able to form iscom structures with cholesterol but, however, has no adjuvant activity, whereas the B2 and B3 components (molecular weights of 1988 and 2150 respectively), which do have an adjuvant activity, form a bond with cholesterol but do not form an iscom-like structure therewith; adjuvant activity is understood to signify that the agent promotes the antibody response and/or cell-mediated immune response. Therefore, according to this WO 90/03184, either whole Quil A or both B4B and B2 or B3 must be used to prepare an iscom structure with cholesterol which has an adjuvant activity.

Since, as already stated above, Quil A has a certain toxic activity and the Quil A components disclosed in WO 90/03184 are not able both to form an iscom structure with cholesterol and have an adjuvant activity, the Applicant has sought other saponins which have a substantially reduced toxicity compared with Quil A and are also able to form an iscom structure having adjuvant activity.

Surprisingly, the Applicant has found that despite the discouraging data in WO 90/03184, there are some Quil A components which meet the requirements described above.

The invention therefore relates to immunogenic complexes, such as two-dimensional lamellae and in particular three-dimensional iscoms, which have an adjuvant activity and are composed of at least one sterol, at least one Quil A component as defined below and, in the case of an iscom, also a phospholipid, as well as, optionally, at least one antigen generating an immune reaction. Of the Quil A components indicated below, the Quil A component designated QA 3 is preferred because this both has a substantially reduced toxicity, or substantially reduced haemolytic activity, compared with Quil A, and also is capable of forming the abovementioned two-dimensional lamellae and iscom structures having an adjuvant activity, using the general preparation techniques known from the prior art.

For the sake of clarity, in the framework of the invention
(a) a two-dimensional lamella is understood to be a two-dimensional structure having a honeycomb structure, which at least is composed of a sterol, a saponin and, optionally, an antigen, and
(b) an iscom is understood to be a three-dimensional spherical cage-like structure having a diameter of 35–200 nm, which at least is composed of a sterol, a saponin, a phospholipid and, optionally, an antigen.

The starting material used for the research carried out by the Applicant, on which the invention is based, was lyophilised Quil A from Iscotec AB, Lulea, Sweden. This product was separated into 23 fractions on a semi-preparative scale. In the chromatographic method employed, the more lipophilic components were eluted later in the chromatogram. Within the framework of the research, these fractions were examined to determine their haemolytic activity, sugar composition, adjuvant action and the capacity for forming "empty" iscoms. The adjuvant action of PIC3 iscoms (PIC3=pore protein I from *Neissaria gonorrhoeae* strain C3) or PIC3 iscom-like structures with one or more Quil A fractions according to the invention was also determined. A similar action was determined for viral F-protein iscoms (F-protein=fusion protein from measles virus).

The research showed that the 23 Quil A fractions possessed stable chromatographic characteristics. Although a single main peak was obtained in all cases, when a chromatographic determination was carried out again in an analytical column using the stationary phase/mobile phase initially employed, it was found from the shape of the peak that one or more ancillary components were probably present in virtually all fractions.

With regard to the chromatographic investigation carried out, it is pointed out that the polar compounds, which elute at the start of the separation and form only a small percentage of the total, had a highly deviating UV spectrum compared with the main peaks. Therefore, no further research was carried out on the fractions which were indicated by these peaks.

The sugar composition and also the aglycone fragment of the Quil A fractions show no significant differences. On the other hand, the relative haemolytic activity varies substantially. As will be seen below, this varies from 5% to 150%, compared with the whole Quil A product.

The adjuvant activity of the Quil A fractions shows no relationship with the polarity or with the sugar composition. All fractions have an adjuvant activity. The lowest (QA 7) and the highest (QA 6) values of the adjuvant action differ by almost a factor of 5.

If, in general, vaccines are administered parenterally, the latter preferably consist of colloidal particles, that is to say particles having a size of less than 200 nm. With particles of such a size it is possible to carry out a sterile filtration step in a relatively simple manner at the end of the production process. Moreover, suspensions of this type are stable, so that a reproducible effect can be guaranteed. Complexes having an average size of less than 200 nm are often prepared using the generally known standard iscom preparation procedures. Various preparations containing QA fractions according to the invention are heterogeneous, as determined by electron microscopy and dynamic light scattering, but all of these preparations contained small complexes having a size of 50–200 nm. It can be deduced from this that it will be possible in a relatively simple manner to produce more homogeneous dispersions containing small complexes if the preparation process itself or the lipid composition are varied, or two or more Quil A components according to the invention are used.

The invention relates in particular to the Quil A component QA 3, which has a very low haemolytic activity and moreover is able to form iscoms with sterols and phospholipids. Iscoms of this type have a low haemolytic activity and the immunogenicity thereof is comparable with that of conventional iscoms (that is to say whole Quil A iscoms).

As can be deduced from the prior art, the saponins must be used in the method according to the invention in at least the critical micelle-forming concentration (CMC). It is assumed that this concentration for Quil A components does not deviate substantially from the CMC of Quil A, which is about 0.03% by weight.

The sterols which can be used in the immunogenic complexes according to the invention are the known sterols of animal or vegetable origin, such as cholesterol, lanosterol, lumisterol, stigmasterol and sitoesterol. According to the invention, the sterol used is preferably cholesterol.

Phosphatidic acid and esters thereof, such as phosphatidylcholine and in particular phosphatidylethanolamine, can be used as phospholipids, which are used in the preparation of iscoms.

In order to form immunogenic complexes which are provided with an antigen protein or peptide, said antigenic protein or peptide must be dissolved in water or solubilised in water. In general, nonionic, ionic or zwitterionic detergents can be used for this purpose. Octyl glucoside and MEGA-10 (decanoyl-N-methylglucamide) can advantageously be used as detergent, although alkylphenylpolyoxyethylene ethers are also suitable, in particular a polyethylene glycol p-isooctylphenyl ether containing 9 to 10 ethylene oxide groups, which, for example, is available commercially under the trade name Triton X-100®.

Any desired antigenic proteins or peptides can be incorporated in the immunogenic complexes according to the invention. These proteins or peptides can be membrane proteins or membrane peptides isolated from viruses, bacteria, mycoplasmas, parasites or animal cells. The proteins or peptides can also be prepared synthetically or with the aid of recombinant DNA techniques and can also be incorporated in purified form in the immunogenic complexes. For purification of an antigenic protein or peptide of natural origin, in addition to ultracentrifugation or dialysis a further purification step is usually carried out, for example a chromatographic purification step, such as on a column containing DEAE-Sephadex or by means of nnmunoaffinity chromatography. If the antigenic proteins or peptides do not contain hydrophobic portions, they must be chemically bonded to a compound containing a hydrophobic fragment, such as, for example, a lipid or the like.

The preparation of the immunogenic complexes according to the invention is in general carried out in such a way that the dissolved or solubilised antigen is brought into contact with a solution which contains the saponin in at least the critical micelle-forming concentration, a sterol and, in the case of an iscom, also a phospholipid. The detergent is then removed and the immunogenic complex formed is purified.

In general, the known methods, such as dialysis, gradient centrifugation or chromatography, can be used for removal of the detergent. If gradient centrifugation and chromatographic methods, for example gel filtration, are used for removal of the detergent, the immunogenic complex is at the same time substantially freed from other substances, such as excess glycoside and sterol. In general, a dialysis is not sufficient for the purification of the immunogenic complexes, although the immunogenic complexes are formed by removal of the detergent by dialysis.

The solutions obtained from the immunogenic complexes can, if desired, be lyophilised in the presence of a cryoprotectant, such as trehalose or lactose. The lyophilised preparations can then be reconstituted for use by adding water.

The invention also relates to pharmaceutical preparations which contain immunogenic complexes obtained with the aid of the present invention. These preparations can be obtained by bringing the immunogenic complexes into a form suitable for parenteral or oral administration. In general, pharmaceutical preparations which are to be administered parenterally contain the immunogenic complexes in an aqueous, physiologically acceptable medium which, if desired, contains a buffer and/or a salt, such as sodium chloride, for adjustment of the osmotic pressure.

The pharmaceutical preparations according to the invention display, in particular when QA 3 is used as the saponin, a substantially reduced haemolytic activity compared with the known pharmaceutical preparations, in which the whole Quil A is present as a component.

LEGEND

FIG. 1: Chromatogram of the semi-preparative separation of Quil A on a Supelcosil LC-18 semi-preparative column. In this Figure the numerals 1–23 represent the 23 QA components of Quil A. The peaks before QA 1 are regarded as impurities. The letters A, B, C and D indicated in this Figure represent the components QA 3 (A), QA 20 (B) and two impurities (C, D); the UV spectra of these four components are illustrated in FIG. 2a–d.

FIG. 2a–d: UV spectra of the components A, B, C and D shown in FIG. 1.

Figure 3:
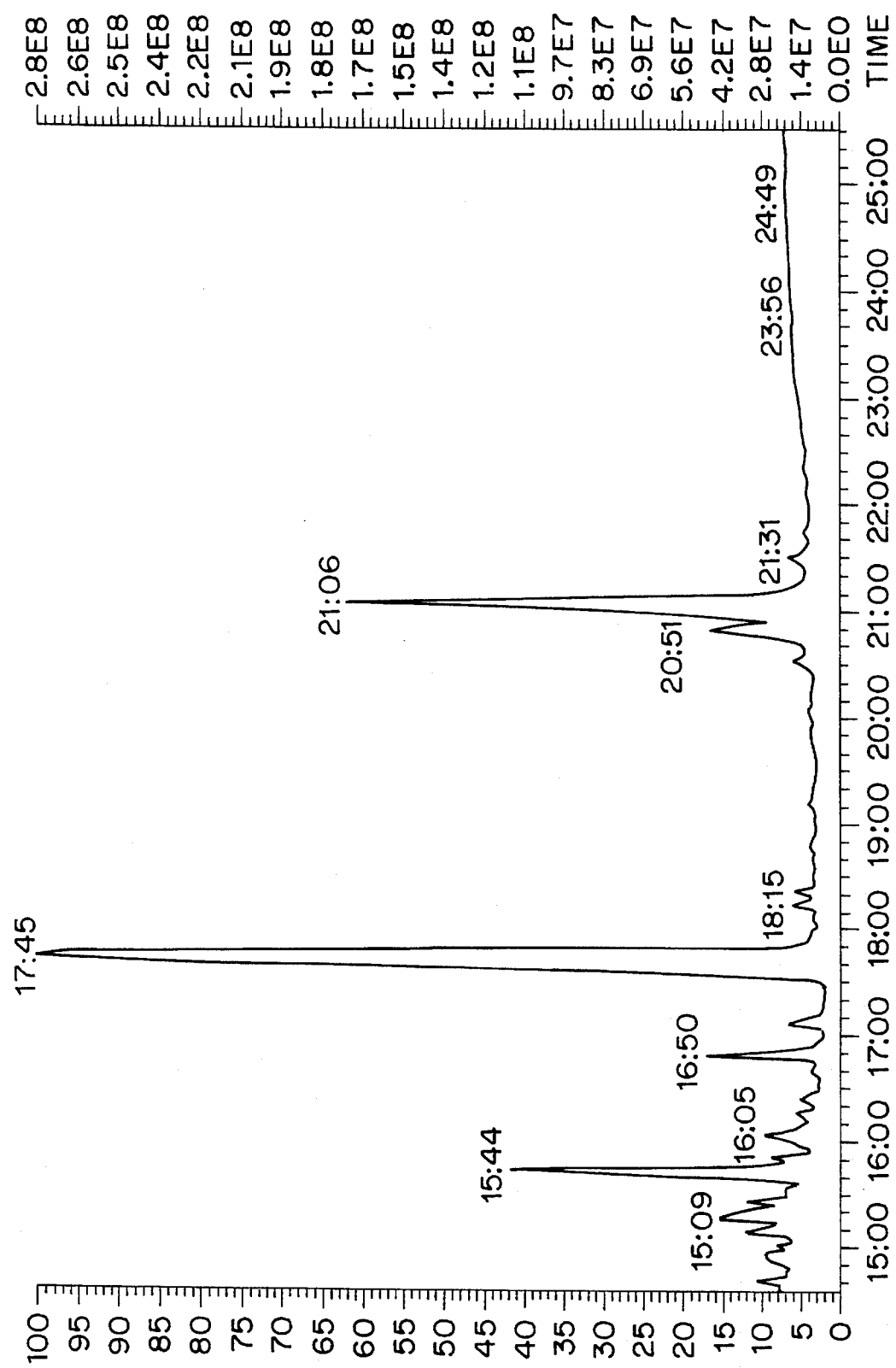

FIG. 3: Gas chromatogram of the methanolysed, silylated QA 3/cholesterol mixture in a CP Sil SCB column (17 m×0.25mm) (Chrompack, The Netherlands).

Figure 4:
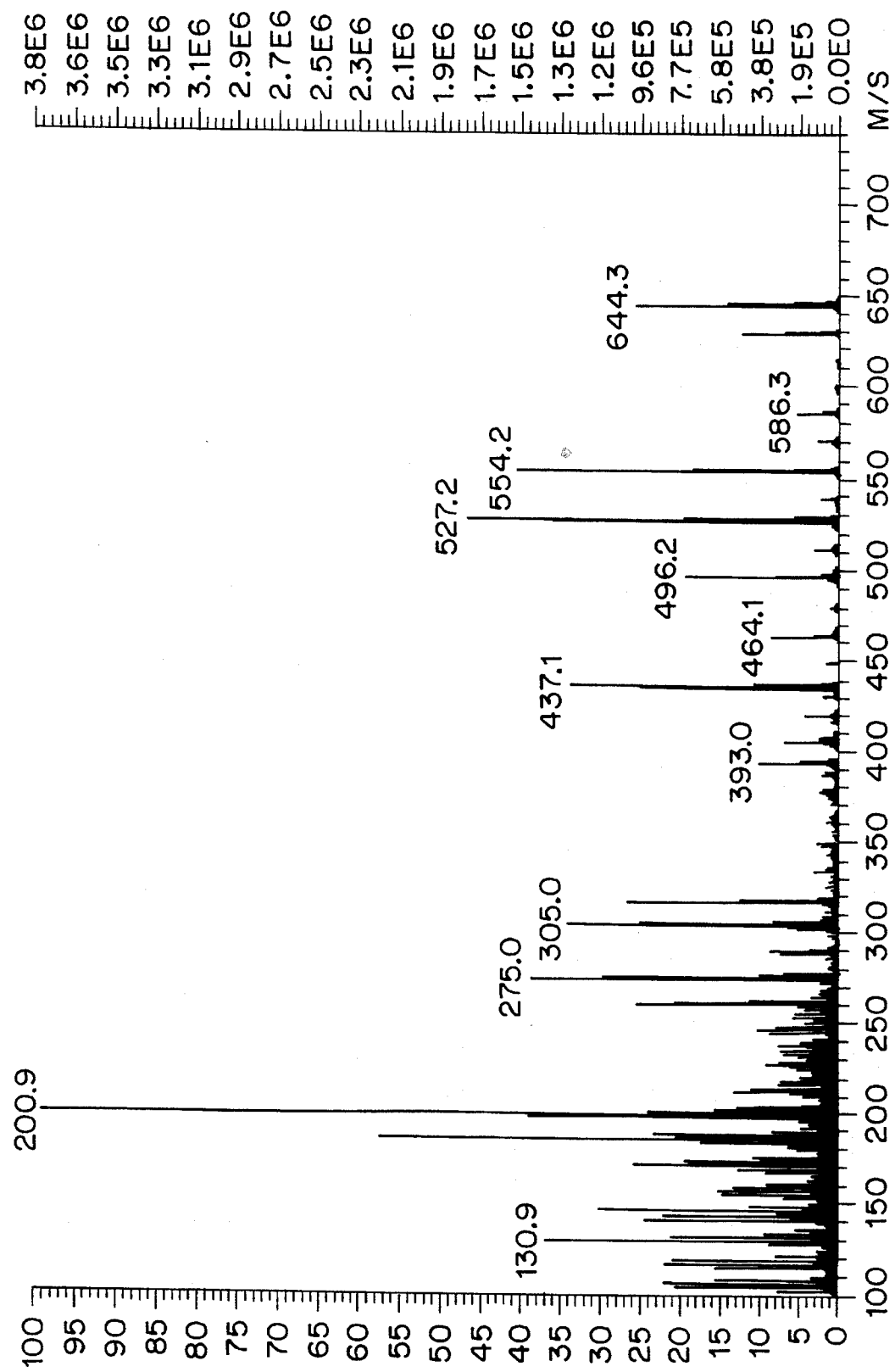

FIG. 4: Mass spectrum of the peak at 21 min 6 sec shown in FIG. 3.

Figure 5:
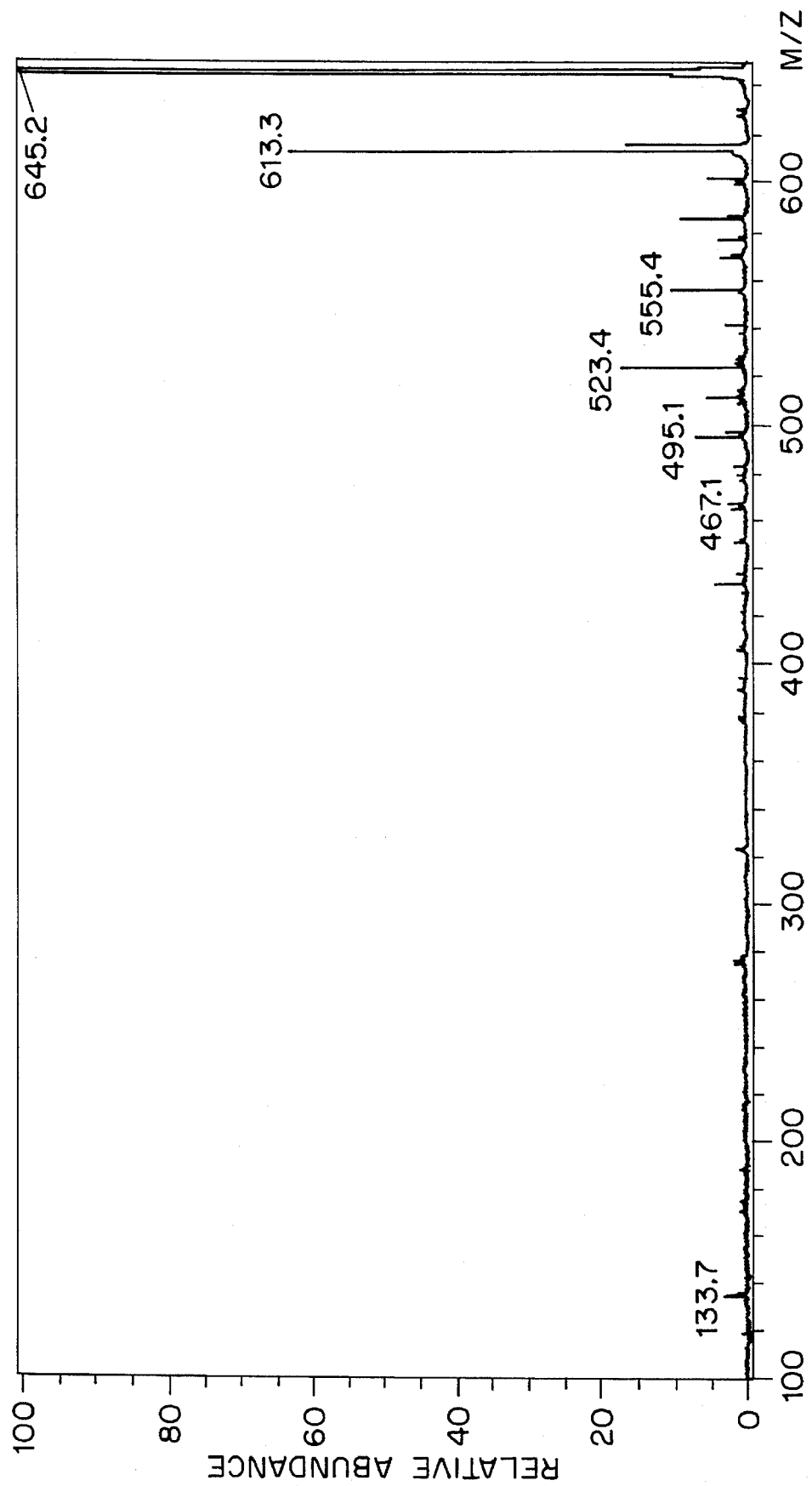

FIG. 5: CAD-MS/MS spectrum of the principal component in the methanolysed, silylated QA 3 fraction. The selected ion is the protonated molecular ion of the corresponding compound in the GC peak at 21 min 6 sec.

Figure 6:
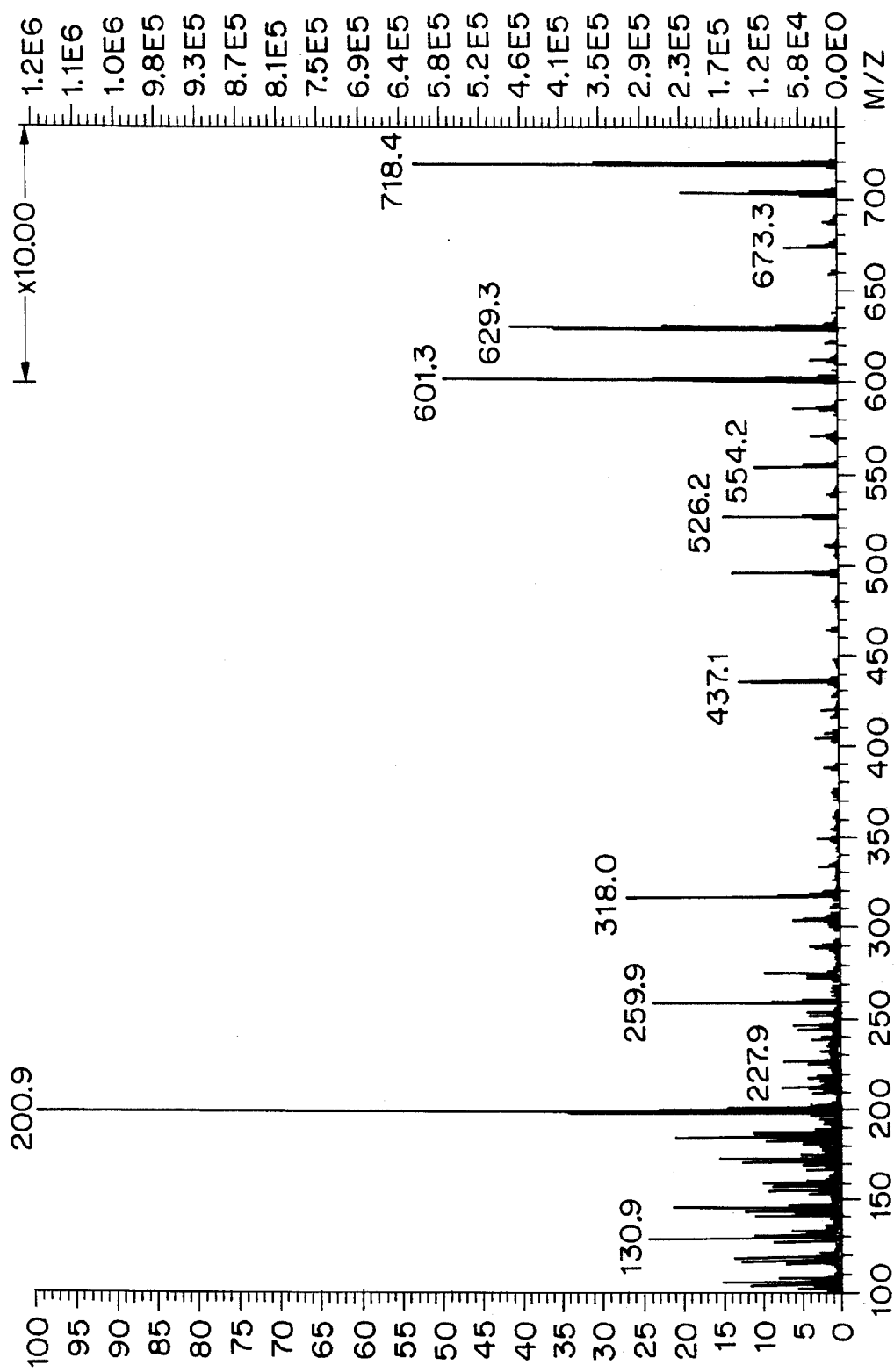

FIG. 6: Mass spectrum of the peak having a retention time of 20 min 51 sec shown in FIG. 3.

The invention is illustrated in more detail with the aid of the experiments described below.

MATERIALS AND METHODS

Separation Procedure

Lyophilised Quil A (Iscotec AB, Lulea, Sweden) was solubilised in water (50 mg/ml). The mixture was separated on a Supelcosil LC-18 semi-preparative column (Supelco, Bellefonte, Pa.) (250×10 mm). The mobile phase consisted of acetonitrile in water, which was buffered with 10 mm ammonium acetate, pH 6.0. The acetonitrile concentration increased from 24 to 44% by volume in the course of 60 min. The flow rate was 2.5 ml/min. The peaks were detected at 206 nm and automatically collected using a Frac 100 fraction collector (Pharmacia LKB, Uppsala, Sweden). The sample size was 500 µl. Approximately 40 separations were carried out, the corresponding peaks being collected and freeze-dried. The water content of 2 lyophilised fractions was determined using an MCI model VA-05 (Mitsubishi). In order to investigate the purity and stability of the collected fractions, all preparations were chromatographed again on an analytical (150×4.6 mm) Supelcosil LC-18 column using the same mobile phase. One batch of QA 1, 2, 4 to 16, 18, 19 and 21 was purified and two batches of QA 3, 17, 20, 22 and 23 were purified.

Sugar Composition

The general sugar composition was determined in the manner described in Kamerling J. P., et al, 1989, Carbohydrates, pp. 175–263, A. M. Lawson (ed.), Clin. Biochem. 1, Mass Spectrometry, W. de Gruyter, New York. About 0.5 mg of sample was methanolysed overnight at 85° C. in 0.5 ml of 1.0M HCl in dry methanol. 100 mmol of mannitol were added to each sample as internal standard. After the methanolysis, the samples were neutralised with $Ag_2CO_3$ and 40 µl of acetic anhydride were added to the samples in order to re-N-acetylate any N-deacetylated carbohydrates present. After standing for 24 hours at room temperature, during which time the samples were protected from light, the samples were centrifuged, the supernatants collected and the $Ag_2CO_3$ pellet washed twice with methanol. The methanol was removed in a Rotavap distillation apparatus under a water-pump vacuum at 35° C. and the residues were dried overnight under a water-pump vacuum in the presence of $P_2O_5$. The sugars were silylated by adding 100 µl of pyridine:hexamethyldisilazane:chlorotrimethylsilane=5:1:1 (v/v/v) for half an hour before the analysis. The samples were analysed on a SE 30 WCOT fused-silica capillary column (25 m×0.32 mm). A flame ionisation detector was used and nitrogen was used as carrier gas. The injection gate temperature and detector temperature were 210° C. and 230° C., respectively. The oven temperature rose from 130° C. to 220° C. at a rate of 4° C./min. A standard mixture of known concentration was used to determine the adjustment factors which correct for the partial destruction of the sugars.

Recovery of the PIC3 protein. (PIC3=pore protein I from Neisseria Gonorrhoea strain C3).

Neisseria gonorrhoea strain C3 was cultured in the conventional manner. The cultures were inactivated by heating at 56° C. for 30 minutes. After centrifugation, the inactivated bacteria were lyophilised. The isolation procedure for the pore protein I (PI) was based on the procedure which was used by Blake and Gotschlich for the isolation of pore protein II (J. Exp. Med. 139, pp. 452–462, 1984). The lyophilised bacteria were extracted with 2.5 g of 3-(N-tetradecyl-N,N-dimethylammonium)-1-propanesulphonate (Z 3–14) in 0.5M $CaCl_2$ at pH=4.0. After one hour, intact cells and fragments were removed by centrifugation (20 min, 20,000×g). Ethanol was added to the supernatant liquor until the concentration was 20%. After 30 minutes, the precipitated material was removed by centrifuging (20 min, 10,000×g). The supernatant liquor was concentrated by ultrafiltration (Amicon hollow fibre cartridge H 10×50); 50 mMTris. HCl, 10 mM EDTA and 0.05% (weight/vol) Z 3–14, pH=8.0 (buffer A) were added and the volume was reduced by half. This procedure was repeated five times in order completely to remove the calcium chloride and the ethanol. The protein solution was then introduced into a DEAE Sepharose column equilibrated with buffer A. The proteins were eluted using a linear gradient of 0.0 to 0.6M NaCl in buffer A. The fractions were analysed with the aid of SDS-PAGE and the PI-containing fractions were combined. The partially purified PI was introduced into a Sephacryl S-300 column previously equilibrated with 50 mMTris-HCl, 200 mM NaCl, 10 mM EDTA and 0.05% (weight/vol) of Z 3–14, pH=7.2. The PI-containing fractions were combined. The resulting product was designated purified PI.

Recovery of the F protein (F=fusion protein of measles virus).

Measles virus (the Edmonston B strain), cultured on Verocells stuck to microcarriers, was purified using conventional methods (P. de Vries: Measles virus iscom; a candidate subunit vaccine, thesis, University of Utrecht, 1988).

The purified virus was stored at −70° C. until used. In order to purify F, concentrated virus was treated with 2% Triton X-100. The insoluble debris was sedimented by means of ultracentrifugation. F was purified by means of immunoaffinity chromatography from the supernatant, which contained solubilised lipids and viral membrane proteins. To this end, an anti-F monoclonal was coupled with CNBr-activated Sepharose 4B. A low-pressure chromatography column was filled with this material. The solubilised material was circulated through the column overnight, the F-protein being bound. After the column had been rinsed with 1% octyl glucoside, the bound F was released with the aid of a buffer containing 5M $NH_4SCN$ and 1% octyl glucoside. Fractions containing F-protein were dialysed.

Preparation of Immunogenic Complexes

The following procedure was used for the incorporation of PI and F in iscoms. A mixture of phosphatidylethanolamine type III-A (=PE) (Sigma) and cholesterol in chloroform (weight ratio PE:cholesterol=1:1) was dried under nitrogen and the resulting lipid film was then solubilised in a TN buffer (Tris/NaCl; 10 mM Tris, 140 mM NaCl, pH=7.4) containing 136 mM octyl glucoside. PI (or F) in the TN buffer containing 136 mM octyl glucoside was then added. The ratio of lipid (PE+cholesterol) to protein (PI or F) was 5:1 (weight/weight). Whole Quil A (Iscotec AB, Lulea, Sweden) or the QA fraction(s) according to the invention in the form of a 10% solution (weight/vol) in water were then added. The ratio of lipid (PE+cholesterol) to Quil A or QA fraction was 1:2 (weight/weight). The lipid concentration was about 1 mg/ml. The iscoms were formed by dialysis against two passages with one liter of TN buffer for at least 24 hours at 4° C. The iscoms were separated off from the non-incorporated components by centrifugation through a 10 to 60% sucrose gradient in TN buffer (18 hours, 50,000×g). In this procedure, the iscom band obtained was removed. In some cases the ultracentrifugation step was omitted.

In order to prepare "empty" iscoms, that is to say iscoms containing no PI, the above procedure was followed except that TN buffer containing 136 mM octyl glucoside was added in place of the solution of PI in TN buffer containing 136 mM octyl glucoside.

Electron Microscope

A negative contrast staining was carried out using 2% phosphotungstic acid ($H_3[P(W_3O_{10})_4]$), which had been adjusted to a pH of 5.2 using KOH.

Determination of the Protein Content

The protein contents of the iscoms were determined via a Bradford protein assay (Bradford M. M., 1976, Anal. Biochem. 72, pp. 248–254).

Determination of the Quil A Content

Quil A and Quil A fractions were determined chromatographically on a Hypersil ODS 5μ analytical column (150× 4.6 mm) (Shahdon, Runcorn, UK). The acetonitrile concentration changed from 32% to 40% in ammonium acetate-buffered water during the analysis. The peaks were detected at 208 nm. A quantification was achieved by measuring the peak height or the height of the three main peaks in the case of Quil A. Standard curves were plotted for calibration purposes.

Hydrodynamic Particle Sizes

This particle size was determined by scattering in monochromatic light using a System 4600 size analyzer (Malvern Instruments Ltd., Worcestershire, UK).

Haemolytic Activity

The haemolytic activity of Quil A fractions and iscoms was determined by the method given in Kersten et al., On the Structure of Immune-stimulating Saponin-lipid Complexes (iscoms), Biochim. Biophys. Acta 1062, 165–171 (1991)). V-shape wells in a microtitration plate were filled with 100 μl of 0.5% (v/v) erythrocytes of Cercopithecus aureus in McIlvain buffer having a pH of 7.2 (13.1 mM citric acid, 173.8 mM $Na_2HPO_4$). 100 μl of the sample or the QA standard (concentration increasing from 0.5 to 8.0 μg/ml) were then added. After an incubation for 3 hours at 37° C., the plate was centrifuged for 5 min at 2000 rpm (Hettich Rotixa IKS, Tuttlingen, Germany) and 100 μl of supernatant were transferred to a flat-bottomed microtitration plate. The extinction at 405 nm was determined using a microtitration plate reader (Titertek Multiskan MCC, Flow Laboratories, Herts., UK).

Adjuvant Activity

The adjuvant activity was tested in mice using the purified pore protein I of Neisseria gonorrhoeae (strain C3) (PIC3) as model antigen. PIC3 was purified in the manner described above with the following modifications: solid phenylmethylsulphonyl fluoride (Serva, Heidelberg, Germany) was added to the extraction buffer, an additional clarification step was carried out by filtration using a 1.2 μm filter (RA Millipore, Bedford, Mass.) for the $CaCl_2$ removal procedure and a second filtration (0.45 μm) was carried out before the DEAE-Sephadex chromatography. The gel filtration step was omitted. Male NIH mice (4 per group) were immunised subcutaneously with 2.5 μg of PIC3 and 20 μg of purified Quil A or 2.5 μg of PIC3 in iscoms. The PIC3 was used in the form of a suspension which had been obtained after ethanol precipitation and suspension of the dried pellet in Tris (10 mM)-buffered saline solution, pH 7.4, with the aid of a brief ultrasonic treatment. Four weeks after the primary immunisation, blood samples were collected and the mice were given a booster injection. Two weeks after the booster, the mice were killed and the relative IgG level in the sera was determined with the aid of ELISA using PIC3 as antigen coating.

Immunogenicity

The immunogenicity of the immunogenic complexes was tested in mice. Male NIH mice (8 per group) were immunised subcutaneously with 2.5 μg or 1 μg of protein (PIC3 or F) in complexes. Four weeks after the primary immunisation, blood samples were collected and the mice were given a booster injection. Two weeks after the booster the mice were killed and the relative IgG level in the sera was determined with the aid of ELISA using PIC3 or F as antigen coating.

Mass Spectrometric Analyses

Positive FAB, negative FAB and CAD-MS/MS spectra were generated on a HX 110/HX 110 tandem mass spectrometer (Jeol, Tokyo, Japan).

RESULTS

Quil A Purification

The chromatogram of the abovementioned semi-preparative separation of Quil A is illustrated in FIG. 1. Initial experiments showed that the peaks at the start of the chromatogram represented a very small percentage by mass. This fragment was therefore no longer included in the further studies carried out by the Applicant.

The first peak which contained an appreciable amount of mass was designated QA 1. In total, 23 peaks and peak groups were identified and collected. The impurities preceding these peaks are not indicated in more detail in FIG. 1.

Fractions QA 1-QA 23 were freeze-dried, which in all cases resulted in a white, snow-like powder. The residual water content of QA 20 and QA 22 was 4.2% and 4.4% respectively. It was assumed that these residual water contents were representative for all freeze-dried samples. A 1% or 10% (w/v) solution in water was prepared from all fractions. The solutions were stored at −20° C.; the lyophilised preparations were stored at 4° C.

When the 23 QA fractions were re-chromatographed there was always only one main peak present, which sometimes was accompanied by a shoulder or a small preliminary peak.

UV Spectra

The spectra of Quil A fractions (QA), as recorded using a diode array detector, were identical (190–370 nm). The fractions absorb only at short wavelengths and are transparent above about 240 nm. The majority of peaks which precede QA 1 have a completely different spectrum with maxima at 200 nm and 280 nm or 310 nm.

Figure 2A:
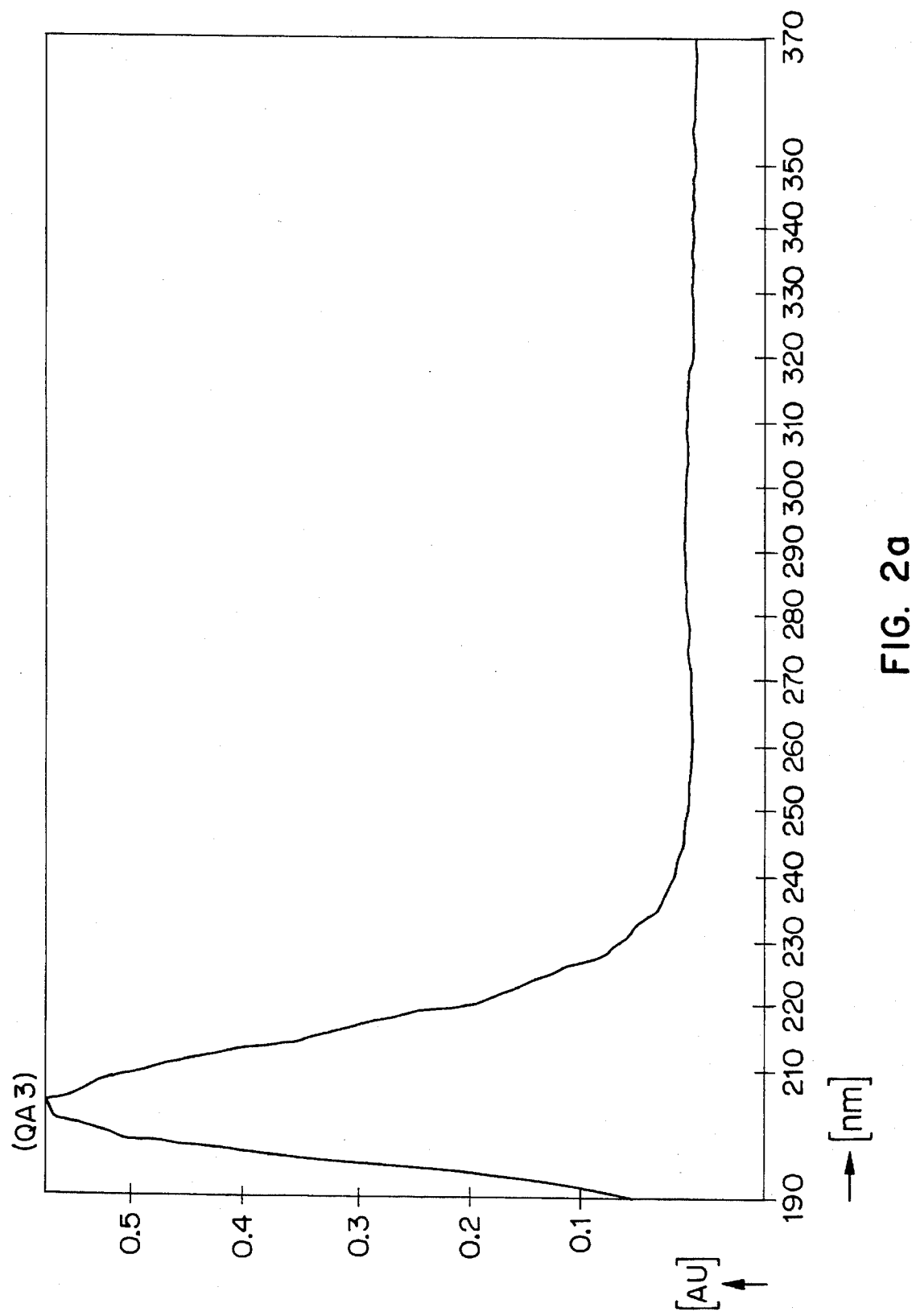
Figure 2B:
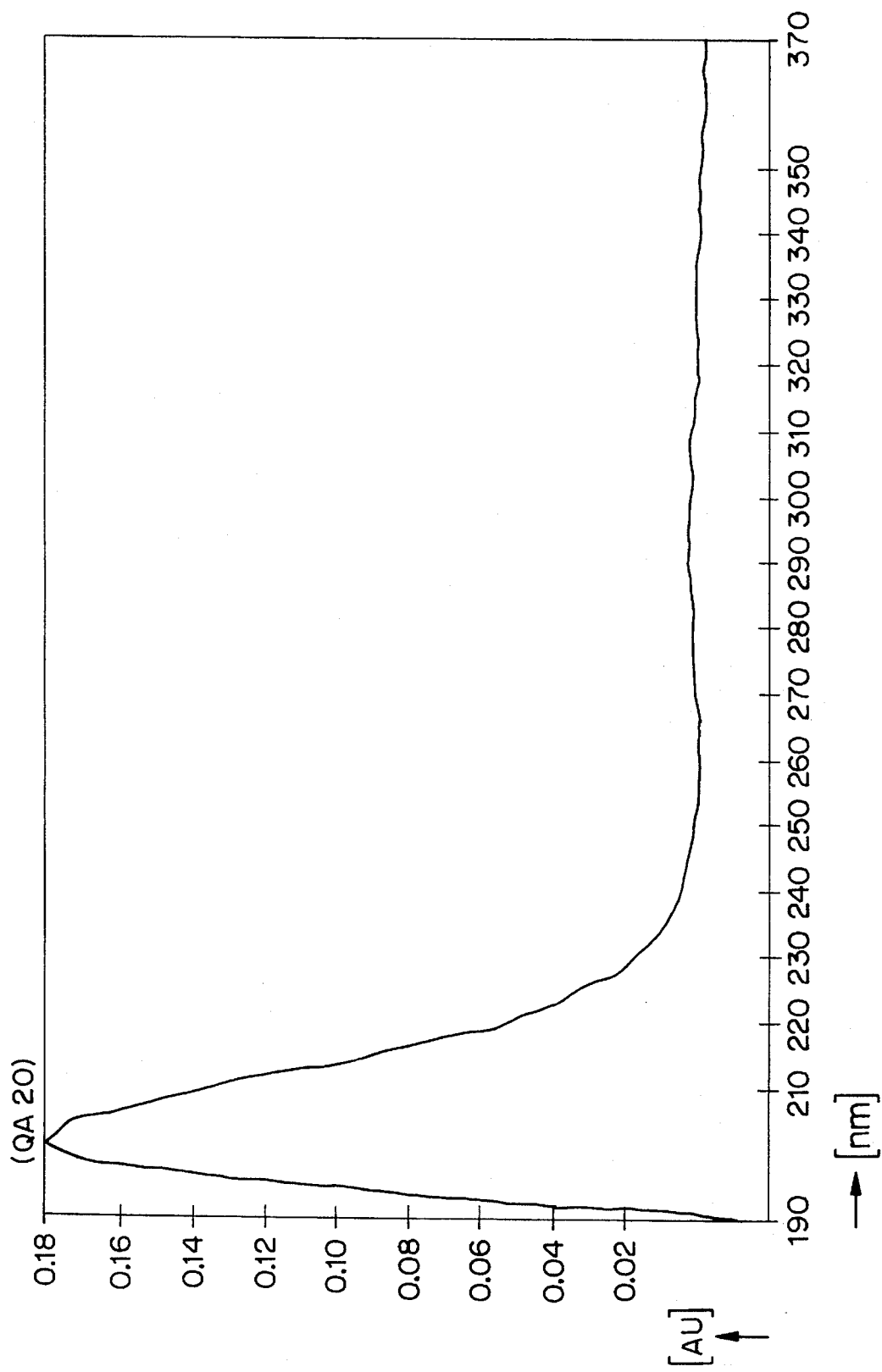
Figure 2C:
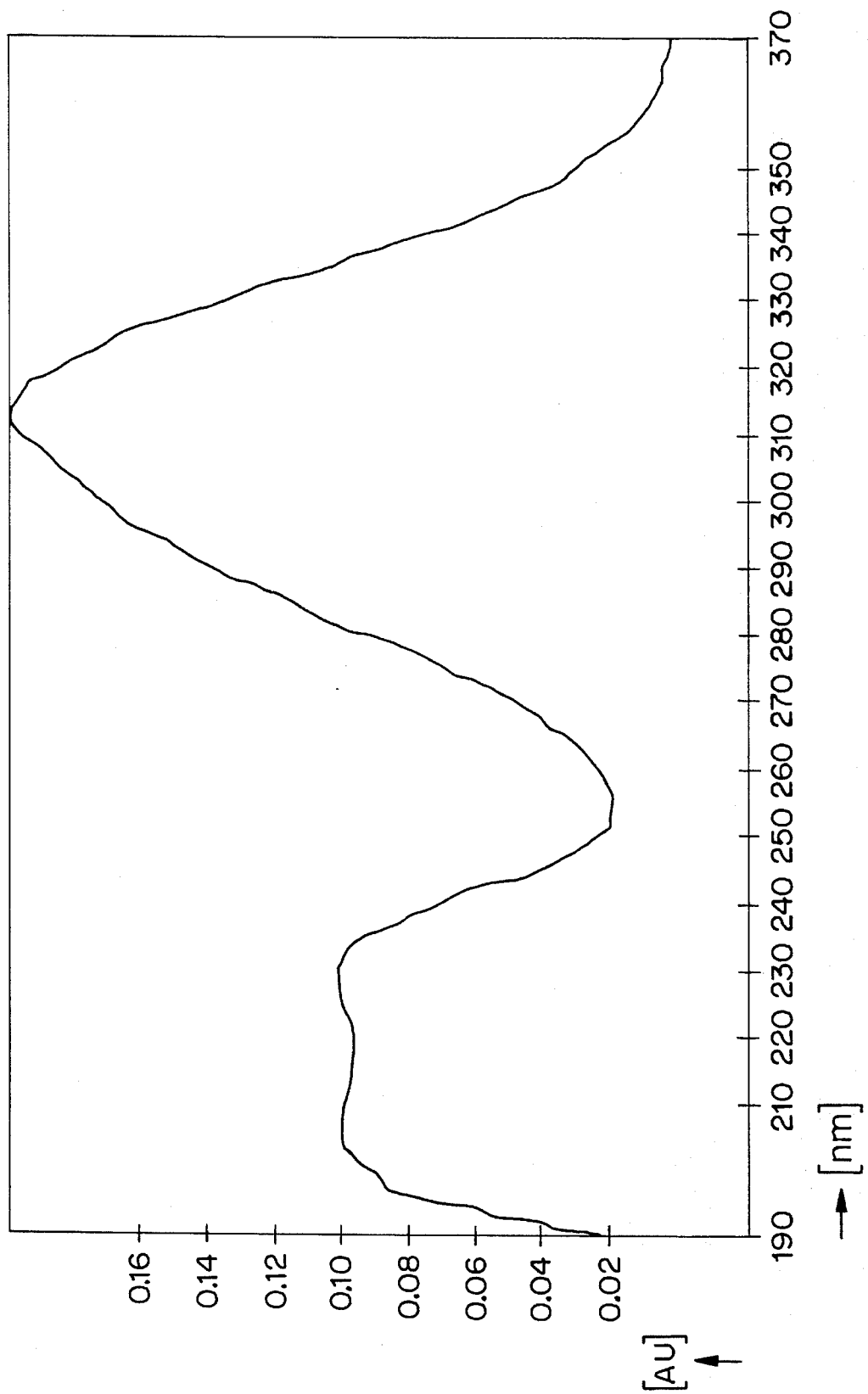
Figure 2D:
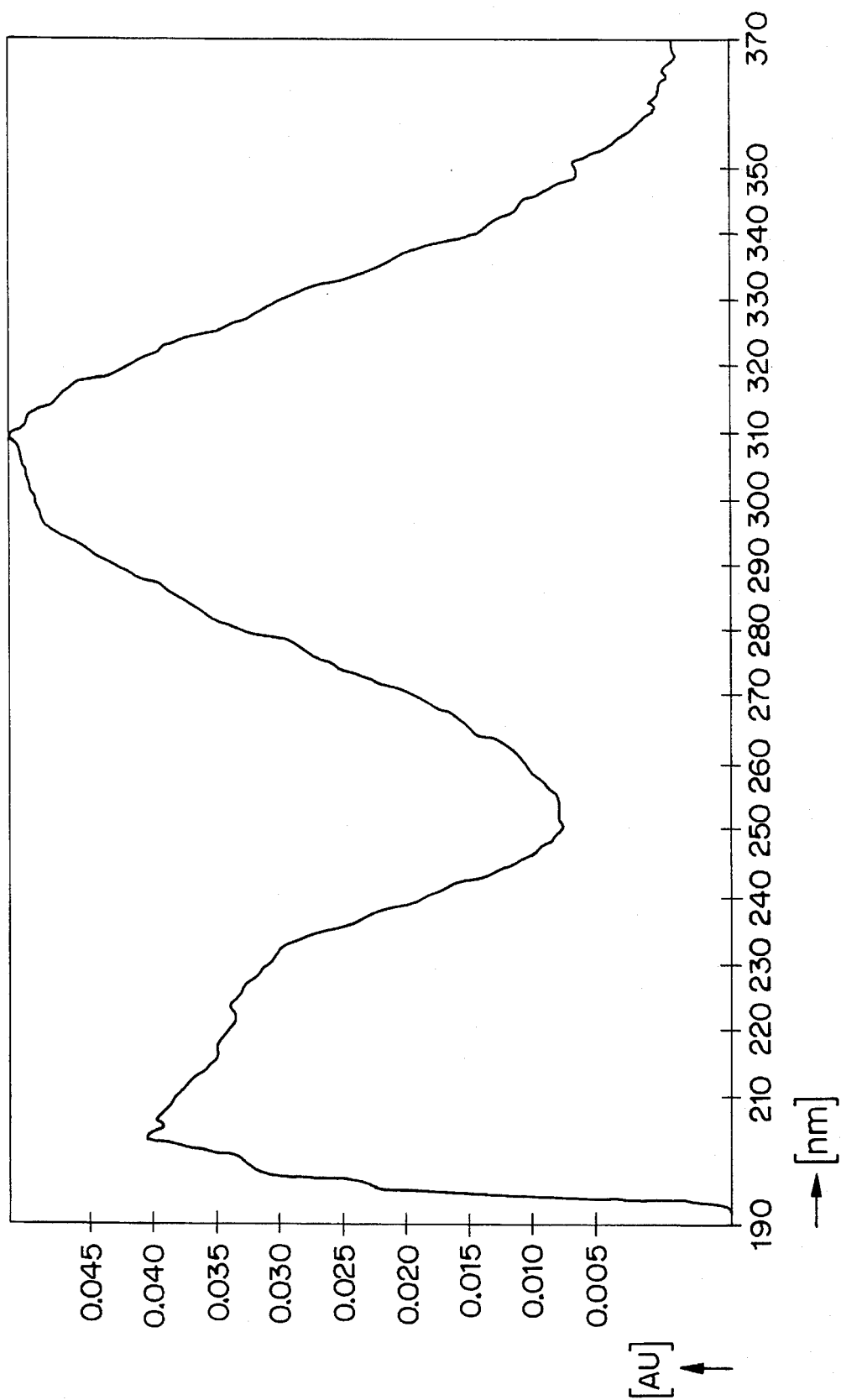

The appended FIG. 2a-3 shows the UV spectra of QA 3 (FIG. 2a) and QA 20 (FIG. 2b) and of the impurities C [indicated in FIG. 1] (FIG. 2c) and D [indicated in FIG. 1] (FIG. 2d).

Sugar Composition

No significant differences were found in the sugar composition of the 23 Quil A fractions as collected by the Applicant (see Table A). Sugars which occur in all fractions are rhamnose, fucose, xylose, glucuronic acid and galactose.

In addition, arabinose and/or glucose were detected in some fractions. The molar ratios vary frequently from 0, 1 or 2. This is probably caused by contamination with other components, as can be deduced from the peak shapes, or by the presence of sugars having identical characteristics on gas chromatography. Furthermore, in this context, it is pointed out that small amounts of, for example, hemicellulose cannot be entirely excluded.

TABLE A

Sugar composition (in molar ratio) of Quil A fractions 1–23 and whole Quil A

| Quil A fraction peak | ara[1] | rham[2] | fuc[3] | xyl[4] | glca[5] | gal[6] | glc[7] |
|---|---|---|---|---|---|---|---|
| 1 | 0.2 | 2.3 | 1.1 | 1.7 | 1.0 | 1.0 | 1.0 |
| 2 | 0.2 | 2.3 | 1.1 | 1.6 | 1.0 | 1.0 | 0.5 |
| 3 | 0.2 | 2.3 | 1.1 | 1.7 | 1.0 | 1.0 | 1.0 |
| 4 | 0.2 | 2.4 | 1.1 | 1.7 | 1.0 | 1.0 | 0.3 |
| 5 | 0.2 | 1.8 | 1.1 | 1.6 | 1.0 | 1.0 | 1.4 |
| 6 | 0.1 | 2.0 | 1.1 | 1.6 | 1.0 | 1.0 | 0.8 |
| 7 | 0.2 | 1.7 | 1.1 | 1.7 | 1.0 | 1.0 | 1.0 |
| 8 | 0.3 | 1.6 | 1.1 | 1.0 | 1.0 | 1.0 | 1.1 |
| 9 | 0.5 | 1.8 | 1.1 | 1.1 | 1.0 | 1.0 | 1.0 |
| 10 | 0.3 | 2.3 | 1.1 | 1.8 | 1.0 | 1.0 | 0.9 |
| 11 | 0.3 | 2.2 | 1.1 | 1.7 | 1.0 | 1.0 | 0.4 |
| 12 | 0.4 | 2.0 | 1.1 | 1.7 | 1.0 | 1.0 | 0.9 |
| 13 | 0.6 | 1.7 | 2.1 | 1.0 | 1.0 | 1.0 | 1.0 |
| 14 | 0.3 | 1.8 | 1.1 | 1.2 | 1.0 | 1.0 | 0.7 |
| 15 | 0.4 | 1.7 | 1.1 | 1.7 | 1.0 | 1.0 | 1.0 |
| 16 | 0.7 | 1.8 | 1.1 | 1.9 | 1.0 | 1.0 | 0.8 |
| 17 | 1.1 | 2.3 | 1.1 | 1.8 | 1.0 | 1.0 | 1.1 |
| 18 | 0.7 | 1.6 | 1.1 | 1.7 | 1.0 | 1.0 | 0.7 |
| 19 | 0.5 | 1.5 | 1.0 | 1.5 | 1.0 | 1.0 | 0.9 |
| 20 | 1.1 | 1.7 | 1.1 | 1.7 | 1.0 | 1.0 | 0.9 |
| 21 | 0.8 | 1.4 | 1.1 | 2.0 | 1.0 | 1.0 | 0.6 |
| 22 | 1.1 | 1.5 | 1.1 | 1.8 | 1.0 | 1.0 | 0.1 |
| 23 | 0.7 | 1.4 | 0.9 | 1.2 | 1.0 | 1.0 | 0.4 |
| Whole QA | 0.8 | 1.7 | 1.0 | 1.5 | 0.9 | 1.0 | 0.8 |

[1] ara = arabinose or a sugar behaving like arabinose
[2] rham = rhamnose or a sugar behaving like rhamnose
[3] fuc = fucose or a sugar behaving like fucose
[4] xyl = xylose or a sugar behaving like xylose
[5] glca = glucuronic acid
[6] gal = galactose = 1.0 defined
[7] glc = glucose or a sugar behaving like glucose Haemolytic Activity The haemolytic activity of the QA 1 to QA 23 fractions of batch 1 and QA 3, 17, 20, 22 and 23 of batch 2 is shown in Table B. It can be deduced from this table that the haemolytic activity increases with decreasing polarity, that is to say the components with longer retention times. The fractions having the shortest retention time have haemolytic activities which are 10 to 20 times lower than those of Quil A.

TABLE B

Relative haemolytic activity of Quil A fractions 1–23 (whole Quil A = 100%)

Haemolytic activity compared with whole Quil A (%)

| Quil A fraction | Batch 1 (n = 1) | Batch 2 (n = 2) |
|---|---|---|
| 1 | 5 | |
| 2 | 8 | |
| 3 | 8 | 32 ± 6 |
| 4 | 14 | |
| 5 | 4 | |
| 6 | 5 | |
| 7 | 5 | |
| 8 | 14 | |
| 9 | 16 | |
| 10 | 16 | |
| 11 | 22 | |
| 12 | 33 | |
| 13 | 38 | |
| 14 | 31 | |
| 15 | 15 | |
| 16 | 56 | |
| 17 | 65 | 78 ± 5 |
| 18 | 36 | |
| 19 | 72 | |
| 20 | 108 | 113 ± 28 |
| 21 | 108 | |
| 22 | 147 | 176 ± 53 |
| 23 | 103 | 140 ± 1 |

Adjuvant Activity of Quil A Fractions 1–23

It can be deduced from this Table that all fractions possess an adjuvant activity.

TABLE C

Adjuvant activity of Quil A fractions 1–23 and whole Quil A

| Quil A fraction | IgG response Serum dilution at A450 = 0.4 in ELISA | |
|---|---|---|
| | primary × $10^2$ | booster × $10^3$ |
| 1 | 3.7 | 2.4 |
| 2 | 4.6 | 4.6 |
| 3 | 6.9 | 5.5 |
| 4 | 6.6 | 3.5 |
| 5 | 2.6 | 2.8 |
| 6 | 1.2 | 5.8 |
| 7 | <1.0 | 1.2 |
| 8 | 4.6 | 2.6 |
| 9 | 1.9 | 2.0 |
| 10 | 1.6 | 1.6 |
| 11 | 2.3 | 2.5 |
| 12 | 8.0 | 2.7 |
| 13 | 3.9 | 2.0 |
| 14 | 3.0 | 4.0 |
| 15 | 3.9 | 1.6 |
| 16 | 2.9 | 1.4 |
| 17 | 5.0 | 1.5 |
| 18 | 1.6 | 2.2 |
| 19 | 3.5 | 3.4 |
| 20 | 2.7 | 1.6 |
| 21 | 2.3 | 4.5 |
| 22 | 2.7 | 2.7 |
| 23 | 2.9 | 1.8 |
| Whole QA | 1.8 | 2.9 |
| No adjuvant | <1.0 | 0.2 |

Adjuvant activity was determined in mice using pore protein I from *Neisseria gonorrhoeae* strain C as antigen; adjuvant dose: 20 μg. Four mice were used per group.

Formation of Immunogenic Complexes

For a number of QA fractions it was not possible directly to prepare lipid/QA complexes having dimensions which approach those of standard iscoms, in which whole Quil A samples are used (Table D).

In the majority of cases (especially in the case of batch 1), a turbid dispersion was obtained using the abovementioned standard iscom formation procedure. However, an electron microscopic study always showed that particles having the typical honeycomb structure had formed, as observed in iscoms. Moreover, a large number of particles having size of an iscom were often present. The "empty" iscoms prepared from QA fractions 1, 3, 5, 6, 9, 12–14, 18 and 23 of batch 1 and QA fractions 17, 22 and 23 of batch 2 had an average particle size of less than 200 nm.

TABLE D

Particle size of protein-free structures, formed after an iscom preparation procedure

| Quil A fraction | Average particle size of empty iscom structure (nm) | |
|---|---|---|
| | Batch 1 | Batch 2[1] |
| 1 | 150 | |
| 2 | >1000 | |
| 3 | 145 | |
| 4 | >1000 | |
| 5 | 148 | |
| 6 | 160 | |
| 7 | >1000 | |
| 8 | >1000 | |
| 9 | 95 | |
| 10 | >1000 | |
| 11 | >1000 | |
| 12 | 124 | |
| 13 | 106 | |
| 14 | 166 | |
| 15 | >1000 | |
| 16 | >1000 | |
| 17 | >1000 | 124, 124, 223 |
| 18 | 97 | |
| 19 | >1000 | |
| 20 | >1000 | 231, >1000 |
| 21 | >1000 | |
| 22 | 838 | 51, 75, 101 |
| 23 | 67 | 55, 65 |
| Whole QA | 53 | 29, 39, 44 |

[1] The various measured values are from (2 or 3) different preparations.

PIC3-containing iscoms were prepared using six Quil A fractions (QA 3, 17, 18, 20, 22 and 23) from batch 1. Following a gradient purification and analysis (see Table E), the immunogenicity thereof was determined. In this context, it was very surprising that PIC3 iscoms containing Quil A fraction QA 3 showed outstanding results. PIC3-containing and F-containing iscoms were also prepared using QA 3 from batch 2. A third series of iscoms was prepared using QA 3, 17, 20, 22 and 23 from batch 2. This latter series, which contained PIC3 or F, was not purified on a sucrose gradient. The immunogenicity of the second and third series of iscoms was determined. For this determination the dosage was reduced to 1 μg of protein (Tables F and G). The results confirm that QA 3 iscoms are equally as immunogenic as whole QA iscoms containing PIC3 as antigen. With F as antigen, QA 3 iscoms appear to be somewhat less immunogenic, especially without gradient purification of the iscoms (Table G).

TABLE E

Analysis and immunogenicity of PIC3-containing iscom-like structures, prepared using 6 Quil A fractions (batch 1) and gradient-purified.

| Preparation | Protein (μg/ml) | Quil A (μg/ml) | Haemolytic activity corresponding to × μg/ml free whole Quil A | Size (nm) | IgG response[1] Serum dilution at A450 = 0.4 in ELISA | |
|---|---|---|---|---|---|---|
| | | | | | primary × $10^3$ | booster × $10^3$ |
| QA 3 iscom | 32 | 299 | 10 | 111 | 1.6 | 19.2 |
| QA 17 iscom | 122 | 1070 | 9 | >1000 | 1.6 | 6.4 |
| QA 18 iscom | 43 | 430 | 13 | >1000 | 0.9 | 4.5 |
| QA 20 iscom | 50 | 775 | 171 | >1000 | 1.3 | 17.9 |
| QA 22 iscom | 92 | 2150 | 339 | >1000 | 1.6 | 7.3 |
| QA 23 iscom | 52 | 883 | 11 | >1000 | 0.6 | 22.3 |
| Whole QA iscom | 28 | 470 | 168 | 65 | 0.5 | 19.2 |

[1] Eight mice per group, 2.5 μg of protein per mouse per immunisation.

TABLE F

Analysis and immunogenicity of PIC3-containing and F-containing iscom-like structures, prepared using QA 3 (batch 2) and gradient-purified.

| Preparation | Protein (µg/ml) | Quil A (µg/ml) | Haemolytic activity corresponding to × µg/ml free whole Quil A | Size (nm) | IgG response[1] Serum dilution 50% A450 max. | |
|---|---|---|---|---|---|---|
| | | | | | primary × 10³ | booster × 10³ |
| QA 3 PIC3 iscom | 75 | 580 | 15 | 45 | 0.9 | 17.0 |
| Whole QA PIC3 iscom | 70 | 800 | 80 | 47 | 2.6 | 20.9 |
| QA 3 F protein | 25 | 65 | <10 | 460 | 0.6 | 2.0 |
| Whole QA F iscom | 10 | n.d.[2] | <10 | 146 | 0.3 | 3.7 |

[1] Eight mice per group, 1 µg of protein per mouse per immunisation.
[2] n.d.: not determined.

TABLE G

Analysis and immunogenicity of PIC3-containing and F-containing iscom-like structures, prepared using 5 Quil A fractions (batch 2) and not gradient-purified.

| Preparation[3] | Haemolytic activity corresponding to × µg/ml free whole QA[1] | Size (nm) | IgG response serum[2] dilution at 50% A450 max | |
|---|---|---|---|---|
| | | | primary × 10³ | booster × 10³ |
| QA 3 PIC3 iscom | 25 | 161 | 0.9 | 17.0 |
| QA 17 PIC3 iscom | <21 | 117 | 1.8 | 17.0 |
| QA 20 PIC3 iscom | 28 | 122 | 1.5 | 24.0 |
| QA 22 PIC3 iscom | 145 | 127 | 0.7 | 25.7 |
| QA 23 PIC3 iscom | 28 | 130 | 1.3 | 17.0 |
| Whole QA | 36 | 126 | 1.5 | 21.9 |
| QA 3 F iscom | 22 | 540 | 0.5 | 4.5 |
| QA 17 F iscom | <21 | 189 | 0.4 | 9.3 |
| QA 20 F iscom | 24 | 230 | 0.2 | 4.0 |
| QA 22 F iscom | 263 | 126 | 0.3 | 4.4 |
| QA 23 F iscom | <21 | 127 | <0.2 | 0.7 |
| Whole QA | 45 | 86 | 0.4 | 10.5 |

[1] Before dialysis preparations contain 1000 µg/ml of Quil A component.
[2] Eight mice per group, 1 µg of protein per mouse per immunisation.
[3] Initial protein content = 100 µg/ml

Mass Spectrometric Analyses

The molecular masses of the MH⁺ ions of the oversize portion of the QA fractions according to the invention are shown in Table H below. This determination of the molecular mass was carried out using a positive FAB-MS method. The Applicant assumes that a sodium ion is enclosed in the sugar fragment bound to carbon atom 28 of the aglycone skeleton. The values shown in Table H should therefore, with a probability bordering on certainty, be reduced by 23.

TABLE H

| Fraction | MH⁺[a] |
|---|---|
| QA 1 | 1744 |
| QA 2 | 1592 |
| QA 3 | 1887 |
| QA 4 | 1723 |
| QA 5 | 1811 |
| QA 6 | 1649, 1693 |
| QA 7 | 1797 |
| QA 8 | 1448, 2190 |
| QA 9 | 1364, 1500, 2335 |
| QA 10 | 1927 |
| QA 11 | 1765 |
| QA 12 | 1972 |
| QA 13 | 2057, 2189 |
| QA 14 | —[b] |
| QA 15 | 1781 |
| QA 16 | —[b] |
| QA 17 | 2319 |
| QA 18 | —[b] |
| QA 19 | 2041 |
| QA 20 | 2173 |
| QA 21 | 2011, 2083 |
| QA 22 | —[b] |
| QA 23 | 2053 |

[a] In all fractions, except for QA 10 and QA 13, MH⁺ + 14 is also present in various ratios with MH⁺. This is the methyl ester of glucuronic acid.
[b] Many masses present.

In the light of the interesting characteristics of the Quil A fraction designated QA 3, a mass spectrometric analysis of the main aglycone was carried out; the saponins in Quil A are glycosides which are composed of an aglycone and one or more sugar tails.

Quillaja acid is regarded as the principal aglycone of saponins which are obtained from the bark of *Quillaja saponaria* Molina.

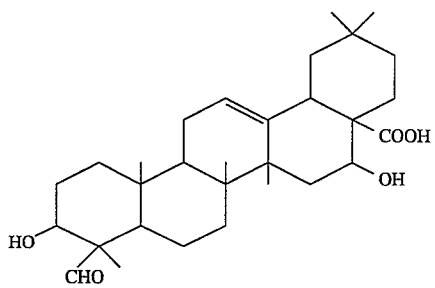

The aglycone fragment of the Quil A fraction QA 3 was analysed with the aid of GC-MS.

A mixture of 0.5 mg of freeze-dried QA 3 and 0.1 mg of cholesterol (Sigma, St. Louis, Mo.) was dissolved 0.5 ml of dry methanol, which contained 1.0M HCl. The methanolysis was carried out for 24 hours at 85° C. The sample was dried at 40° C. under a stream of nitrogen. 100 µl of silylating agent (bis(trimethylsilyl)trifluoro-acetamide:N-trimethylsilylimidazole:trimethylchlorosilane=3:3:2) (weight/weight/weight) were added to the dried residue. The sample was mixed thoroughly and stored in a glass tube at −20° C. until the analysis was carried out. The sugars and the aglycone were separated on a CP Sil SCB column (17 m×0.25 mm) (Chrompack, Middelburg, The Netherlands) using a film thickness of 0.14 µm. The injector temperature was 275° C. and the column temperature increased at a rate of 10° C./min from 70° C. to 310° C. The injection volume was 1.0 µl. The peaks were detected on an Autospec mass spectrometer (VG, Manchester, U.K.). The ionisation took place by means of electron impact (70 eV electrons, ion source temperature: 250° C.). The "step" current was 100 µA and the resolution was 1000 (10% valley). The scan parameters were: magnetic scan of 100 to 1000 mass units at 2 sec/decade. The cycle time was 2.5 s. The silylated aglycone was further analysed using impact-induced fragmentation tandem mass spectrometry (CAD-MS/MS) on a HX110/HX110 mass spectrometer (JEOL, Tokyo, Japan). Positive FAB was used for the desorption/ionisation of the sample by using the JEOL Xe atom canon, used at 6 kV. The instrument was used at an accelerating voltage of 10 kV. The matrix used was glycerol/thioglycerol (1/1) (weight/weight). High energy impact-induced MS/MS spectra were obtained by introducing He gas into the collision cell at base potential, so that the ionic energy in the impact region was 10 keV. The pressure of the impact gas was adjusted such that the response of the precursor ion to the end detector was reduced to ¼ of the non-impact-induced response. The scan range was 55–650 atomic mass units and the cycle time was 1 min 52.8 sec.

For confirmation of the sample preparation and the GC-MS analysis, a commercially available saponin, β-escein (Sigma), having a known chemical structure was analysed. According to the label, the product was 90–95% pure. The gas chromatogram of methanolysed, silylated β-escein showed various peaks having retention times which were longer than those of cholesterol. The mass of the component in the main peak was calculated as 488 (this is without the TMS (trimethylsilyl) groups). This is the recorded mass of the lactone form of the aglycone of β-escein.

The gas chromatogram of the QA 3/cholesterol mixture is shown in FIG. 3. The peak having the retention time of 17 min 45 sec is cholesterol (mass spectrum not illustrated). The peaks which precede cholesterol are sugar derivatives. The mass spectrum of the peak at 21 min 6 sec is illustrated in FIG. 4. The molecular ion has an m/z of 644.3. The molecular isotope cluster indicates the presence of 2 TMS groups. The precise mass of the MH$^+$ ion is 645.4371±0.0028 atomic mass units. The elemental composition which best corresponds to this mass is $C_{37}H_{65}O_5Si_2$, assuming that only C, H, O and 2 Si atoms are present in the molecule. The calculated mass of $C_{37}H_{65}O_5Si_2$ is 645.4370 atomic mass units. The molecular weight of the molecule without the 2 TMS groups is 644–(2×72)–500 atomic mass units ($C_{31}H_{48}O_5$). Quillaja acid ($C_{30}H_{46}O_5$) has a molecular weight of 486. Since the aglycone is obtained by methanolysis, the compound having a mass of 500 may be the methyl ester of quillaja acid. This is confirmed by a tandem mass spectrometric analysis of the silylated aglucone (FIG. 5), which illustrates the loss of methanol (Table I).

TABLE I

Interpretation of the MS/MS spectrum of methanolysed silylated QA 3, with MS 2 at 645 atomic mass units.

| m/z | | Interpretation |
|---|---|---|
| 645 | MH$^+$ | |
| 615 | −30 | (formaldehyde) |
| 613 | −32 | (methanol) |
| 601 | −44 | (ethanol or propane) |
| 585 | −60 | (methyl formate) |
| 569 | −44–32 | |
| 555 | −90 | (HOTMS) |
| 541 | −60–44 | |
| 523 | −32–90 | |
| 511 | −44–90 | |

The ester formation also explains why only 2 TMS groups are present after the silylation. The GC-MS spectrum (FIG. 4) shows the loss of 117 atomic mass units, which can represent a COOTMS group (Table J).

TABLE J

Interpretation of the mass spectrum in FIG. 4

| m/z | Interpretation | |
|---|---|---|
| 644 | M | |
| 629 | M−15 | 15 =CH$_3$ |
| 586 | M−58 | 58 = Si(CH$_3$)$_2$ |
| 554 | M−90 | 90 = HO-TMS$^1$ |
| 527 | M−117 | 117 = COOTMS |
| 496 | M−(90 + 58) | |
| 464 | M−(2 × 90) | |
| 437 | M−(117 + 90) | |

$^1$TMS = Si(CH$_3$)$_3$

This is not in accordance with the methyl ester form of quillaja acid. The fragment is not detected in the MS/MS spectrum. Possibly the presence of a co-eluting impurity is the cause.

M/z 305 is a well-known OTMS fragment of saccharides. It represents the OTMS derivative fragment at $C_2$-$C_3$-$C_4$. It is, however, improbable that in this case m/z 305 originates from the sugar fragment. The fragment probably represents a portion of the aglucon.

A comparison of the GC peak at 21 min 6 sec with a spectrum of the narrow preceding GC peak at 20 min 56 sec shows a remarkable correspondence (FIG. 6). The spectra are similar from m/z 629, which indicates substantial correspondence in both compounds. The difference lies only in the molecular ion region; this is 74 atomic mass units. The difference can be explained by assuming that a C═O group in the compound of the main peak has been reduced to a OH group in the compound of the narrower peak, 2 amu in molecular weight being gained. This OH group is converted to an O-TMS group during the procedure for formation of the derivative, an additional 72 atomic mass units being gained. Therefore, it is probable that the GC peaks at 20 min 56 sec and 21 min 6 sec represent two compounds, one of which is the reduced form of the other.

Furthermore, the conclusions given below can be drawn from a mass spectrometric structural analysis of a sample of intact QA 3:

1. 2 compounds are shown in the sample. The compounds are closely related: one compound is a methyl-substituted form of the other. The elemental compositions and the molecular masses are given in the Table below.

| Elemental composition | $C_{83}H_{130}O_{46}$ | $C_{84}H_{132}O_{46}$ |
|---|---|---|
| MW (monoisotopic) in amu | 1862.8 | 1876.8 |
| MW (average) in amu | 1863.9 | 1878 |

2. Mass spectrometric analysis of the compound having MW=1862.8 leads to the following structure:

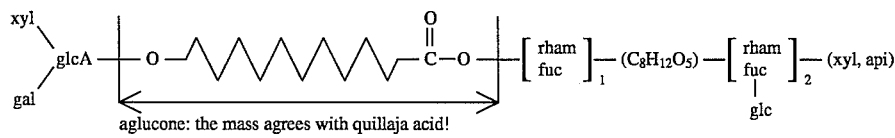

where:

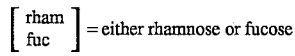
= either rhamnose or fucose

-(xyl,api)=both xyl and api, but in unknown order and: if

is rham, then

is fuc, and vice versa.

3. The possible structures as indicated under point 2 can be assigned a form which leads to a structure which largely agrees with the structure as proposed by Higuchi R. et al (1987), Structure of Desacylsaponins obtained from the Bark of Quillaja Saponaria, Phytochemistry 1987; pp. 229–235 (see FIG. 4). The difference between this and the structure found by us is a group having the elemental composition $C_8H_{12}O_5$.

4. MS analysis of the compound of MW=1876.8 amu indicates that the position of methyl substitution must be in the left-hand sugar group, that is to say in xyl, gal or glcA. At present it is not yet possible to specify this more precisely.

We claim:

1. An immunogenic complex in the form of an iscom comprising at least one sterol, at least one phospholipid and at least one Quil A fraction derived from Quil A hydrophobic interaction chromatography, wherein said Quil A fraction exhibits adjuvant activity and reduced toxicity relative to Quil A, and wherein said Quil A fraction is selected from the group consisting of fractions having the designations QA1, 3, 5, 6, 9, 12, 13, 14, 17, 18, 20 and 23.

2. The immunogenic complex according to claim 1 wherein said at least one Quil A fraction is fraction QA3.

3. The immunogenic complex according to claim 1 comprising QA3 and QA17.

4. The immunogenic complex according to claim 1, wherein said immunogenic complex also contains at least one antigenic protein or peptide containing a natural or synthetically introduced hydrophobic fragment.

5. The immunogenic complex according to claim 4 wherein said antigenic proteins or peptides are membrane proteins or peptides that are synthetic or isolatable selected from the group consisting of viruses, bacteria, mycoplasmas, parasites, and animal cells.

6. A pharmaceutical composition comprising an immunogenic complex according to claim 4 and a pharmaceutical acceptable carrier.

7. A Quil A fraction derived from Quil A by hydrophobic interaction chromatography wherein said fraction is selected from the group consisting of fractions having the designations QA1, 3, 5, 6, 9, 12, 13, 14, 17, 18, 20 and 23.

8. A method of preparation of QA fractions having the designations QA1, 3, 5, 6, 9, 12, 13, 14, 17, 18, 20 and 23 comprising:

dissolving Quil A in water;

separating said Quil A in the resulting solution in a semi-preparative hydrophobic interaction column using an acetonitrile/water solution, buffered in a pH of 6, as mobile phase; and recovering the separated fractions having the designations QA1, 3, 5, 6, 9, 12, 13, 14, 17, 18, 20 and 23.

9. A kit comprising the immunogenic complex according to claim 1 and one or more antigenic proteins or peptides having a natural or synthetically introduced hydrophobic fragment.

10. Quil A fraction having the designation QA 3, which has a MW (monoisotopic) determined via FAB/MS of 1862.8, which compound has the following structure:

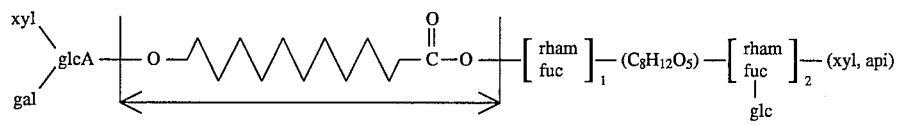

where:

$\begin{bmatrix} \text{rham} \\ \text{fuc} \end{bmatrix}$ = either rhamnose or fucose -(xyl,api)=both xyl and api, but in unknown order and:
 if $\begin{bmatrix} \text{rham} \\ \text{fuc} \end{bmatrix}_1$ is rham, then $\begin{bmatrix} \text{rham} \\ \text{fuc} \end{bmatrix}_2$ is fuc, and vice versa,
wherein said fraction forms iscoms, and exhibits adjuvant activity and reduced toxicity.

* * * * *

UNITED STATES PATENT AND TRADEMARK OFFICE
CERTIFICATE OF CORRECTION

PATENT NO. : 5,620,690
DATED : April 15, 1997
INVENTOR(S) : Kersten et al.

It is certified that error appears in the above-indentified patent and that said Letters Patent is hereby corrected as shown below:

Col. 3, line 34, "sitoeterol" should read --sitosterol--;

Col. 3, line 63, "nnmunoaffinity" should read --immunoaffinity--;

Col. 5, line 58, "139" should read --159--;

Col. 16, line 21, "OA 3" should read --QA 3--;

Col. 18, line 18, "pharmaceutical" should read --pharmaceutically--.

Signed and Sealed this

Twenty-fifth Day of November, 1997

Attest:

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 5,620,690
DATED : April 15, 1997
INVENTOR(S) : Gideon F.A. Kersten, et al.

It is certified that error appears in the above-identified patent and that said Letters Patent is hereby corrected as shown below:

On the title page, item [75] "Der Werken" should read --De Werken--.

Signed and Sealed this

Seventeenth Day of March, 1998

BRUCE LEHMAN

*Attest:*

*Attesting Officer*     *Commissioner of Patents and Trademarks*